(12) United States Patent
Sokawa et al.

(10) Patent No.: US 6,982,081 B2
(45) Date of Patent: Jan. 3, 2006

(54) COMPOSITION FOR TREATMENT OF AND METHOD OF MONITORING HEPATITIS C VIRUS USING INTERFERON-TAU

(75) Inventors: Yoshihiro Sokawa, Kyoto (JP); Chih-Ping Liu, San Francisco, CA (US)

(73) Assignee: Pepgen Corporation, Alameda, CA (US)

( * ) Notice: Subject to any disclaimer, the term of this patent is extended or adjusted under 35 U.S.C. 154(b) by 0 days.

(21) Appl. No.: 09/910,406

(22) Filed: Jul. 19, 2001

(65) Prior Publication Data

US 2003/0049277 A1 Mar. 13, 2003

Related U.S. Application Data

(60) Provisional application No. 60/219,128, filed on Jul. 19, 2000.

(51) Int. Cl.
*A61K 38/21* (2006.01)

(52) U.S. Cl. .................................................. 424/85.4
(58) Field of Classification Search ................. 424/85.4
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,766,068 A | 8/1988 | Oeda et al. | |
| 4,769,238 A | 9/1988 | Rutter et al. | |
| 5,942,223 A | * 8/1999 | Bazer et al. | 424/85.4 |
| 6,372,206 B1 | * 4/2002 | Soos et al. | 424/85.4 |

FOREIGN PATENT DOCUMENTS

| WO | WO 94/10313 | 5/1994 |
|---|---|---|
| WO | WO96/35789 | 11/1996 |
| WO | WO00/78266 | 12/2000 |

OTHER PUBLICATIONS

Kondili et al (Journal of Viral Hepatitis 7:184–195, 2000).*
Arase et al (Journal of Gastroenterology 35:221–225, 2000).*
Zielinska et al. Archivum immunologiae et therapiae experimentalis (Poland) 1996, 44 (5–6) p. 359–66 (abstract only cited).*
Zielinska et al. Archivum immunologiae et therapiae experimentalis (Poland) 1993, 41 (3–4) p. 253–7 (abstract only cited).*
Bartol, F.F., et al., "Characterization of proteins produced in vitro by bovine endometrial explants" *Biology of Reproduction, 33:*745–759 abstract only (1985).
Bazer, F.W. and Johnson, H.M., "Type I Conceptus Interferons: Maternal Recognition of Pregnancy Signals and Potential Therapeutic Agents" *AJRI, 26:*19–22 (1991).

Choo, Q.–L., et al., "Isolation of a cDNA Clone Derived from a Blood–Borne Non–A, Non–B Viral Hepatitis Genome" *Science, 244:*359–362 (1989).
Choo, Q.–L., et al., "Genetic organization and diversity of the hepatitis C virus" *Proc. Natl. Acad. Sci. USA, 88:*2451–2455 (1991).
Cotler, S.J., et al., "Pretreatment symptoms and dosing regimen predict side–effects of interferon therapy for heaptitis C" *Journal of Viral Hepatitis, 7:*211–217 (2000).
Cross, J.C., et al., "Constitutive and trophoblast–specific expression of a class of bovine interferon genes" *Proc. Natl. Acad. Sci. USA, 88:*3817–3821 (1991).
Dieperink, E., et al., "Neurophychiatric Symptoms Associated With Hepatitis C and Interferon Alpha: A Review" *Am. J. Psychiatry, 157:*867–876 (2000).
Ecker, D.J., et al., "Increasing Gene Expression in Yeast by Fusion to Ubiquitin" *Journal of Biological Chemistry, 264*(13):7715–7719 (1989).
Gnatek, G.G., et al., "Maternal Recognition of Pregnancy in the Goat: Effects of Conceptus Removal on Interestrus Intervals and Characterization of Conceptus Protein Production during Early Pregnancy" *Biology of Reproduction, 41:*655–663 (1989).
Helmer, S.D., et al., "Identification of bovine trophoblast protein–1, a secretory protein immunologically related to ovine trophoblast protein–1" *J. Reprod. Fert., 79:*83–91 (1987).
Imakawa, K., et al., "Interferon–like sequence of ovine trophoblast protein secreted by embryonic trophectoderm" *Nature, 330:*377–379 (1987).
Imakawa, K., et al., "Molecular Cloning and Characterization of Complementary Deoxyribonucleic Acids Corresponding to Bovine Trophoblast Protein–1: A Comparison with Ovine Trophoblast Protein–1 and Bovine Interferon–$\alpha_{II}$" *Molecular Endocrinology, 3:*127–139 (1989).
Jarpe, M.A., et al., "Predicted structural motif of IFN$_\tau$" *Protein Engineering, 7*(7):863–867 (1994).
Jiménez–Sáenz, M., et al., "Sustained response to combination therapy in a patient with chronic hepatitis C and thrombocytopenia secondary to α–interferon" *Journal of Gastroenterology and Hepatology, 15:*567–569 (2000).

(Continued)

*Primary Examiner*—Mary E. Mosher
(74) *Attorney, Agent, or Firm*—Judy M. Mohr; Perkins Coie LLP

(57) ABSTRACT

A method of monitoring treatment of HCV by oral administration of ovine IFN-τ is disclosed. The method includes measuring the blood levels of 2',5'-oligoadenylate synthetase prior to and after such oral administration, and if necessary, adjusting the dose of IFN-τ until a measurable increase in blood 2',5'-oligoadenylate synthetase level, relative to the level observed prior to administration, is observed. Also disclosed are oral-delivery compositions for use in treating HCV in an HCV-infected patient comprising ovine IFN-τ, in a dosage effective to stimulate bloodstream levels of 2',5'-oligoadenylate synthetase.

9 Claims, 6 Drawing Sheets

OTHER PUBLICATIONS

Magrin, S., et al., "Hepatitis C Viremia in Chronic Liver Disease: Relationship to Interferon-α or Corticosteroid Treatment" *Hepatology, 19:*273–279 (1994).

Ott, T.L., et al., "Cloning and Expression in *Saccaromyces cerevisiae* of a Synthetic Gene for the Type–I Trophoblast Interferon Ovine Trophoblast Protein–1: Purification and Antiviral Activity" *Journal of Interferon Research, 11:*357–364 (1991).

Pawlotsky, J.–M., et al., "Activity of the Interferon–Induced 2',5'–Oligoadenylate Synthetase in Patients with Chronic Hepatitis C" *Journal of Interferon and Cytokine Research, 15:*857–862 (1995).

Roberts, R.M., et al., "Interferons as Hormones of Pregnancy" *Endocrine Review, 13*(3):432–452 (1992).

Saito, H., et al., "Immunological and virological predictors of outcome during interferon–α therapy of chronic hepatitis C" *Journal of Viral Hepatitis, 7:*64–74 (2000).

Shindo, M., et al., "Elevated Levels of 2',5'–Oligoadenylate Synthetase Activity in Peripheral blood Mononuclear Cells and Serum during Acute Exacerbation of Chronic Hepatitis B" *Hepatology, 9*(5):715–719 (1989).

Trepo, C., "Genotype and viral load as prognostic indicators in the treatment of hepatitis C" *Journal of Viral Hepatitis, 7:*250–257 (2000).

Tyring, S.K., "Introduction to Clinical Uses of Interferons" *Interferon: Principles and Medical Applications,* Baron, et al. (eds.), Galveston TX, 1992.

Vallet, J.L., et al., "The Effect of Ovine Trophoblast Protein–One on Endometrial Protein Secretion and Cyclic Nucleotides" *Biology of Reproduction, 37:*1307–1316 (1987).

Whaley, A.E., et al., "Identification and Cellular Localization of Unique Interferon mRNA from Human Placenta" *Journal of Biological Chemistry, 269*(14):10864–10868 (1994).

Clayette, P., et al., "IFN—tau, a new interferon type I with antiretroviral activity," *Pathologie Biologiel, 47:4 553–559 (1999).*

Saez–Royuela, F., et al., "Treatment of Chronic Non–A Non–B Hepatitis with High Doses of Recombinant IFN–ALPHA or Recobinant IFN–TAU," 40th Annual Meeting of the American Association for the Study of Liver Diseases, Chicago, IL, *Hepatology,* 10:4 646 (1989).

* cited by examiner

COMPOSITION FOR TREATMENT OF AND METHOD OF MONITORING HEPATITIS C VIRUS USING INTERFERON-TAU

This application claims priority to U.S. Provisional application Ser. No. 60/219,128, filed Jul. 19, 2000 and Japan Application No. 2000-317160 filed Oct. 17, 2000, both of which are expressly incorporated by reference herein.

FIELD OF THE INVENTION

The present invention relates to the composition for treatment of conditions relating to hepatitis caused by hepatitis C virus (HCV) infection using Interferon-τ (IFN-τ). The present invention also relates to a method of monitoring treatment of HCV by measuring the blood levels of 2',5'-oligoadenylate synthetase.

REFERENCES

Ausubel, F. M., et al., in *CURRENT PROTOCOLS IN MOLECULAR BIOLOGY*, John Wiley & Sons, Inc., Media, Pa. (1988).

Balzarini, J, et al., *Biochem. Biophys. Res. Commun.* 178:563–569 (1991).

Bartol, F. F., et al., *Biol. Reprod.* 33:745–759 (1985).

Bayne, M. L. et al., *Gene* 66:235–244 (1988).

Bazer, F. W., and Johnson, H. M., *Am. J. Reprod. Immunol.* 26:19–22 (1991).

Bazer, F. W., et al., PCT publication WO/94/10313, published 11 May, 1994.

Beames, et al., *Biotechniques* 11:378 (1991).

Benvegnu, L., et al., *Cancer* 83:901–909 (1998).

Berenguer M., et al., *Adv. Gastroenterol. Hepatol. Clin. Nutr.* 1:2–21 (1996).

Charlier, M., et al., *Mol. Cell Endocrinol.* 76:161–171 (1991).

Choo, Q.-L., et al., *Science* 244, 359–362 (1989).

Choo, Q.-L., et al., *Proc. Natl. Acad. Sci. U.S.A.* 88, 2451–2455 (1991).

Clarke, B. E., *Baillieres Best Pract. Res. Clin. Gastroenterol.* 14:293–305 (2000).

Cotler, S. J., et al., *J. Viral Hepatitis* 7:211–217 (2000).

Cross, J. C., and Roberts, R. M., *Proc. Natl. Acad. Sci. USA* 88:3817–3821 (1991).

Di Bisceglie, A. M., et al., *Hepatology* 16:649–654 (1992).

Dieperink, E., et al., *Am. J. Psychiatry* 157:867–876 (2000).

Ecker, D. J., et al., *J. Biol. Chem.* 264:7715–7719 (1989).

Feher, Z., et al., *Curr. Genet.* 16:461 (1989).

Fernandez H., et al., *Eur. J. Epidemiol.* 2:1–14 (1986).

Godkin, J. D., et al., *J. Reprod. Fertil.* 65:141–150 (1982).

Gnatek, G. G., et al., *Biol. Reprod.* 41:655–664 (1989).

Hitzeman, R. A., et al., U.S. Pat. No. 4,775,622, issued Oct. 4, 1988.

Helmer, S. D., et al., *J Reprod. Fert.* 79:83–91 (1987).

Horiike N., et al., *C. Oncol. Rep.* 5:1171–1174 (1998).

Houglum, *Clin. Pharm.* 2:20–28 (1983).

Imakawa, K., et al., *Nature* 330:377–379 (1987).

Imakawa, K., et al., *Mol. Endocrinol.* 3:127 (1989).

Jarpe, M. A., et al., *Protein Engineering* 7:863–867 (1994).

Jimenez-Saenz, M., et al., *J. Gastroenterology and Hepatology* 15:567–569 (2000).

Klemann, S. W., et al., *Nuc. Acids Res.* 18:6724 (1990).

Koskinas J., et al., *J. Med. Virol.* 45:29–34 (1995).

Lechner, F., et al., *J Exp. Med.* 191:1499–1512 (2000).

Ludwig, D. L., et al., *Gene* 132:33 (1993).

Magrin, S., et al., *Hepatology* 19, 273–279 (1994).

Maniatis, T., et al., in *MOLECULAR CLONING: A LABORATORY MANUAL*, Cold Spring Harbor Laboratory, Cold Spring Harbor, N.Y. (1982).

Martal., J., et al., *J. Reprod. Fertil.* 56:63–73 (1979).

Martin, E. W., in *DISPENSING OF MEDICATION: A PRACTICAL MANUAL ON THE FORMULATION AND DISPENSING OF PHARMACEUTICAL PRODUCTS* (Mack Publishing Co., Easton, Pa.), 1976.

Mullis, K. B., U.S. Pat. No. 4,683,202, issued 28 Jul. 1987.

Mullis, K. B., et al., U.S. Pat. No. 4,683,195, issued 28 Jul. 1987.

Oeda, K., et al., U.S. Pat. No. 4,766,068, issued Aug. 23, 1988.

Ott, T. L., et al., *J. IFN Res.* 11:357–364 (1991).

Pawlotsky, J-M., et al., *J. Interferon and Cytokine Res.* 15:857–862 (1995).

Pearson, W. R. and Lipman, D. J., *PNAS* 85:2444–2448 (1988).

Pearson, W. R., *Methods in Enzymology* 183:63–98 (1990).

Reilly, P. R., et al., *BACULOVIRUS EXPRESSION VECTORS: A LABORATORY MANUAL*, 1992.

Roberts, R. M., et al., *Endocrin. Rev.* 13:432–452 (1992).

Rutter, W. J., et al., U.S. Pat. No. 4,769,238, issued Sep. 6, 1988.

Saito, H., et al., *J. Viral Hepatitis* 7:64–74 (2000).

Sambrook, J., et al., in *MOLECULAR CLONING: A LABORATORY MANUAL*, Second Edition, Cold Spring Harbor Laboratory, Cold Spring Harbor, N.Y. (1989).

Shaw, K. J., et al., *DNA* 7:117 (1988).

Shen, L. P., et al., *Sci. Sin.* 29:856 (1986).

Shindo, M., et al., *Hepatology* 9:715–719 (1989)

Smith, P. K., et al., *Anal. Biochem.* 150:76 (1985).

Stewart, H. J., et al., *Mol. Endocrinol.* 2:65 (1989).

Trepo, C., *J. Viral Hepatitis* 7:250–257 (2000).

Tyring, et al., Interferon: Principles and Medical Applications, 1st Edition, Section VIII., pgs 399–408, 1992.

Vallet, J. L., et al., *Biol. Reprod.* 37:1307 (1987).

Whaley, A. E., et al., *J. Biol. Chem.* 269:10864–10868 (1994).

Wu, D. A., et al., *DNA* 10:201 (1991).

BACKGROUND OF THE INVENTION

Hepatitis C virus (HCV) is a major public health problem affecting an estimated 170 million people worldwide and more than 10% of the population in some countries (Lechner, et al., 2000). HCV is transmitted primarily by transfusion of infected blood and blood products (Cuthbert, et al., 1994; Mansell, et al., 1995). The Centers for Disease Control and Prevention estimate that HCV is responsible for 160,000 new cases of acute hepatitis in the United States each year. Therefore, an urgent medical need exists for an effective anti-HCV agent.

HCV is a positive-stranded, lipid-enveloped RNA virus of the Flaviviridae family, approximately ten thousand nucleotides in length (Choo, et al., 1989). HCV, unlike hepatitis B virus, has no DNA intermediate, and therefore cannot be integrated into the host genome (Berenguer, et al., 1996). Although HCV has been cloned, the virus has been difficult to culture in vitro (Trepo, 2000). HCV is extremely persistent, producing a chronic infection in 85% of infected individuals, although the mechanism of this persistence is unknown (Trepo, 2000).

Treatment of HCV is aimed at reducing inflammation and liver cell damage, thus preventing cirrhosis and hepatocellular carcinoma (Horiike, et al., 1998; Benvegnu, et al., 1998). Therapies that are currently available for HCV are only effective for a small subpopulation of infected patients (Magrin, et al., 1994; Choo, et al., 1991; Choo, et al., 1989). IFN-α was introduced as therapy for chronic hepatitis C in the United States in 1991 and in Japan in 1992 (Saito, et al., 2000). However, use of IFN-α in sufficient dosage to yield clinical efficacy (i.e., at amounts of about $1 \times 10^6$ units/treatment and above) is usually associated with a "flu-like" syndrome characterized by fever, headache, lethargy, arthalgias and myalgias (Tyring, et al., 1992). At doses of $5-10 \times 10^6$ units/treatment and above, other toxicities, such as nausea, vomiting, diarrhea and anorexia, become more frequent. Neuropsychiatric symptoms have also been reported in association with IFN-α treatment (Dieperink, et al., 2000). In addition, some studies suggest that the efficacy of IFN-α treatment is not dose dependent (Saito, et al., 2000), and that treatment with IFN-α is associated with the development or exacerbation of autoimmune disorders in patients with neoplasms or viral hepatitis (Jimenez-Saenz, et al., 2000).

Ribavirin (1-β-D-ribofuranosyl-1,2,4-triazole-3-carboxamide) is a purine nucleoside analogue that has been found to interfere with viral mRNA synthesis and to inhibit in vivo and in vitro replication of a wide range of RNA and DNA viruses (Fernandez, et al., 1986; Balzarini, et al., 1991). Ribavirin has been shown to be efficient in normalizing aminotransferase levels, but has minor activity on serum HCV RNA titres in chronic hepatitis C patients (Di Bisceglie, et al., 1992). Even the beneficial effects of ribavirin, however, are transient (Clarke, 2000; Koskinas, et al., 1995), and because of severe side effects, ribavirin, in combination with IFN-α, can be difficult to tolerate (Cotler, et al., 2000).

Because of the shortcomings associated with current HCV treatment methods, the inventors have set out to identify a new therapeutic candidate that will have more potent antiviral activity and less severe side effects.

SUMMARY OF THE INVENTION

In one aspect, the invention includes an oral-delivery composition for use in treating HCV in a HCV-infected patient. The composition includes ovine Interferon-tau (OvIFN-τ), in a dosage effective to stimulate levels of 2',5'-oligoadenylate synthetase (OAS) observed in the bloodstream 24 hours after administration of the composition. In one embodiment the composition also includes an oral-delivery vehicle containing IFN-τ and effective to release the IFN-τ in active form in the stomach. The composition provides a preferred dose of ovine IFN-τ between $10^8$–$10^{10}$ units.

The composition provides a preferred dose of ovine IFN-τ between $10^{8-10^{10}}$ units. In one embodiment, the dosage of ovine IFN-τ is greater than $1 \times 10^8$ Units/day. In another embodiment, the dosage of ovine IFN-τ is greater than $2 \times 10^8$ Units/day. In yet another embodiment, the dosage of ovine IFN-τ is greater than $4 \times 10^8$ Units/day. In yet, still another embodiment, the dosage of ovine IFN-τ is greater than $1 \times 10^9$ Units/day. The dosage of ovine IFN-τ can be greater than $4 \times 10^9$ Units/day. Preferably, the dosage of ovine IFN-τ is greater than $7 \times 10^9$ Units/day.

In another aspect, the composition for treating HCV in a HCV-infected individual comprises ovine IFN-τ in a form that reaches the stomach, but not the tunica mucosa oris and at a dose effective to induce 2',5'-oligoadenylate synthetase levels measured in the blood 24 hours after oral administration of the composition. A preferred dose is between about $10^8$–$10^{10}$ units.

In still another aspect, the composition of the invention includes ovine IFN-τ as an effective ingredient, where the composition avoids the absorption of ovine IFN-τ through the tunica mucosa oris.

In related aspects, a composition of the invention is for the treatment of hepatitis caused by HCV comprises ovine IFN-τ as an effective ingredient, and a 2',5'-oligoadenylate synthetase activity inducer in animals other than sheep comprising ovine IFN-τ.

In still another aspect, the invention includes a method of monitoring treatment of HCV by oral administration of ovine IFN-τ. The method includes measuring the blood levels of 2',5'-oligoadenylate synthetase prior to and after such oral administration, and if necessary, adjusting the dose of IFN-τ until a measurable increase in blood 2',5'-oligoadenylate synthetase level, relative to the level observed prior to administration, is observed.

These and other objects and features of the invention will become more fully apparent when the following detailed description is read in conjunction with the accompanying drawings.

DETAILED DESCRIPTION OF THE INVENTION

I. Definitions

Hepatitis C virus or HCV refers to the viral species of which pathogenic types cause Non-A Non-B Hepatitis (NANBH), and attenuated types or defective interfering particles derived therefrom. The HCV genome is comprised of RNA. RNA containing viruses have relatively high rates of spontaneous mutation reportedly on the order of $10^{-3}$ to $10^{-4}$ per incorporated nucleotide. Since heterogeneity and fluidity of genotype are inherent in RNA viruses, there are multiple types/subtypes, within the HCV species which may be virulent or avirulent. The propagation, identification, detection, and isolation of various HCV types or isolates is documented in the literature.

Treating a condition refers to administering a therapeutic substance effective to reduce the symptoms of the condition and/or lessen the severity of the condition.

Oral refers to any route that involves administration by the mouth or direct administration into the stomach or intestines, including gastric administration.

OAS level refers to the concentration or activity of blood 2',5'-oligoadenylate synthetase (OAS) protein.

Recombinant host cells, host cells, cells, cell lines, cell cultures, and other such terms denoting microorganisms or higher eukaryotic cell lines cultured as unicellular entities, are used interchangeably, and refer to cells which can be, or have been, used as recipients for recombinant vector or other transfer DNA, and include the progeny of the original cell transfected. It is understood that the progeny of a single parental cell may not necessarily be completely identical in morphology or in genomic or total DNA complement as the original parent, due to accidental or deliberate mutation. Progeny of the parental cell which are sufficiently similar to the parent to be characterized by the relevant property, such as the presence of a nucleotide sequence encoding a desired peptide, are included in the progeny intended yb this definition, and are covered by the above terms.

Operably linked refers to a juxtaposition wherein the components so described are in a relationship permitting them to function in their intended manner. A control sequence operably linked to a coding sequence is ligated in such a way that expression of the coding sequence is achieved under conditions compatible with the control sequences.

An open reading frame is a region of a polynucleotide sequence which encodes for a polypeptide.

Figure 4:
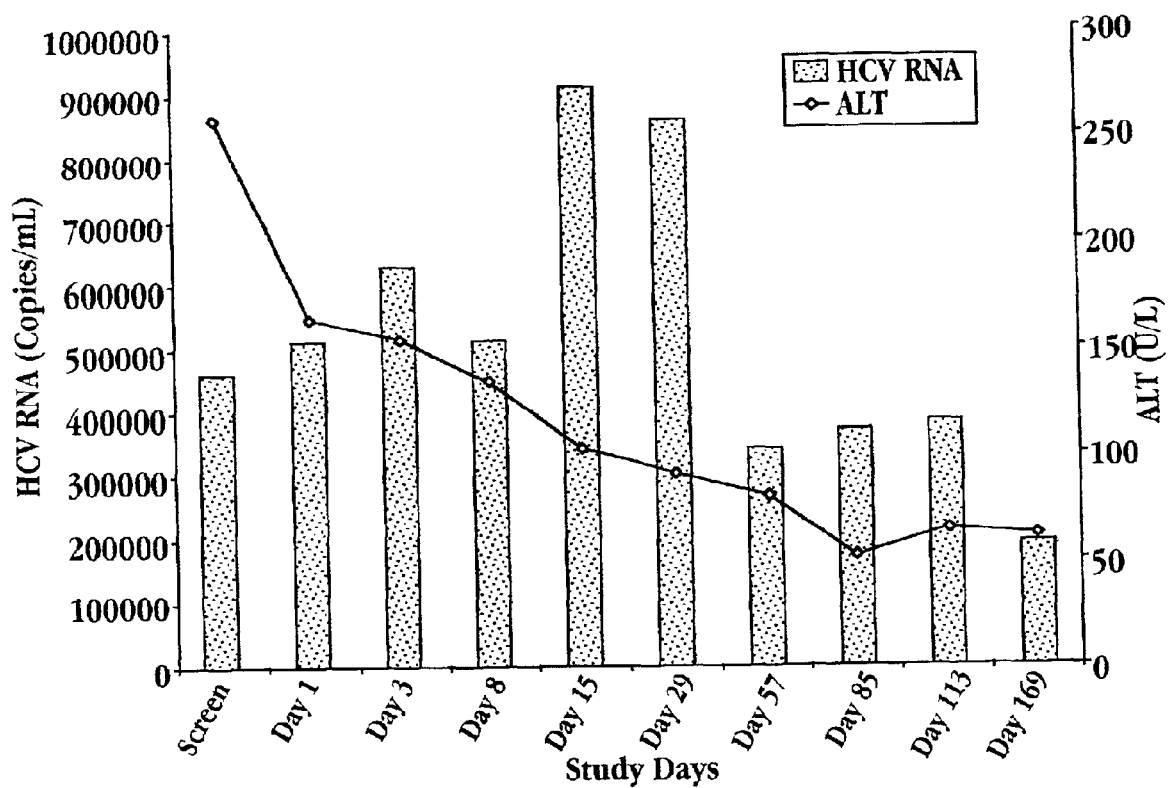
Figure 5:
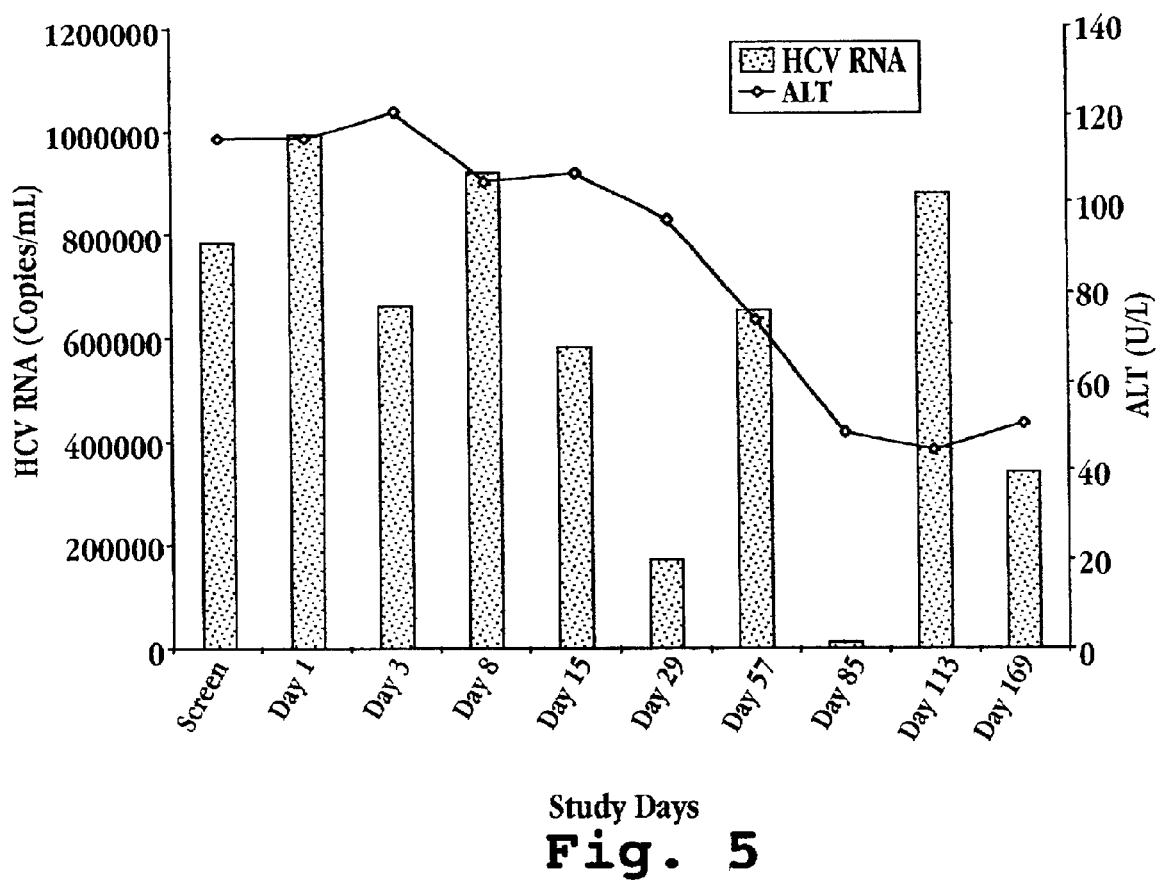
Figure 6:
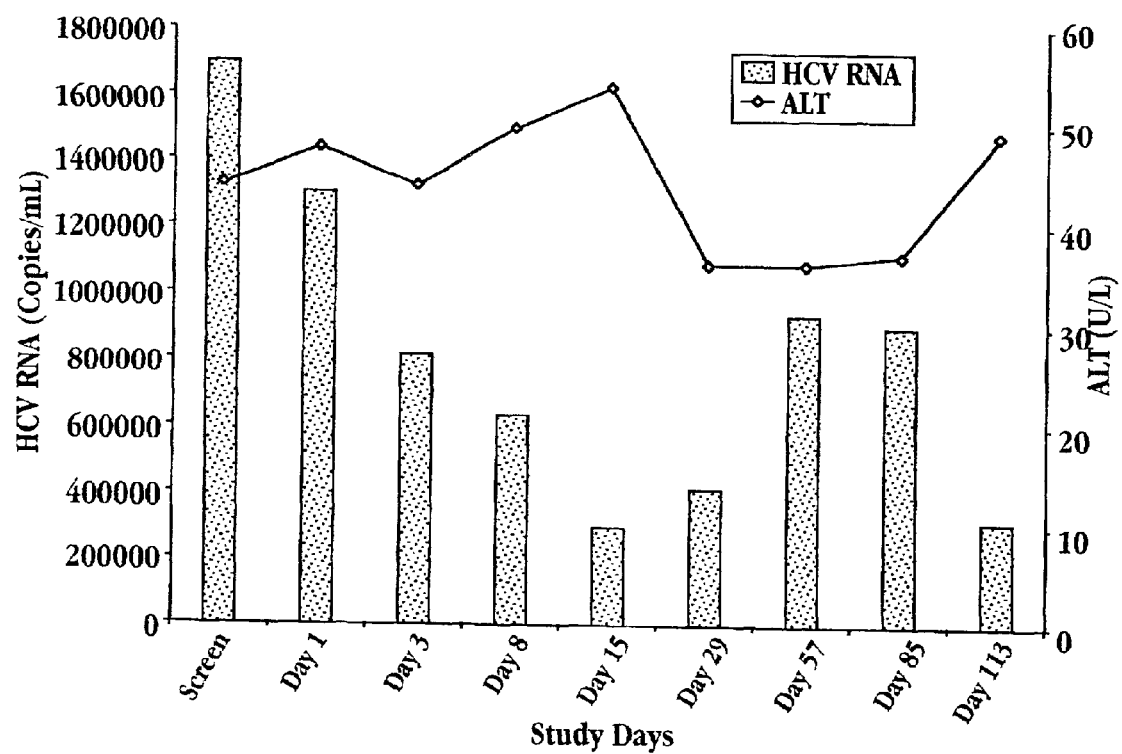
FIGS. 6 and 7 illustrate HCV RNA and ALT levels in two human patients following oral administration of $1.5 \times 10^9$ units/day ovIFN-τ.
Figure 7:
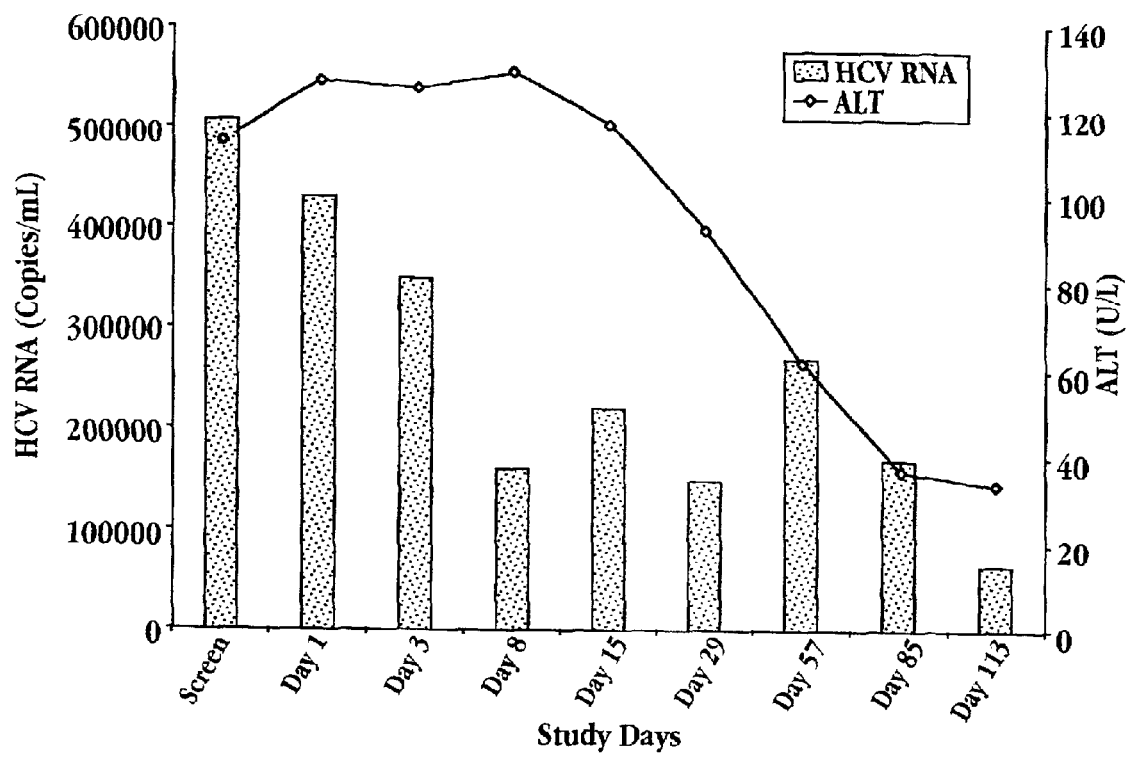

Ovine IFN-τ (ovIFN-τ) refers to a protein having the amino acid sequence as shown in FIG. 4, and to proteins having amino acid substitutions and alterations such as neutral amino acid substitutions that do not significantly affect the activity of the protein. Preferably the sequence includes the ovine IFN-τ sequence of FIG. 4 and the proteins with 90% sequence homology to the sequence shown in FIG. 4. Amino acid homology can be determined using, for example, the ALIGN program with default parameters. This program is found in the FASTA version 1.7 suite of sequence comparison programs (Pearson and Lipman, 1988; Pearson, 1990; program available from William R. Pearson, Department of Biological Chemistry, Box 440, Jordan Hall, Charlottesville, Va.).

II. Interferon-τ

The first IFN-τ to be identified was ovine IFN-τ (OvIFN-τ), as a 18–19 kDa protein. Several isoforms were identified in conceptus (the embryo and surrounding membranes) homogenates (Martal., et al., 1979). Subsequently, a low molecular weight protein released into conceptus culture medium was purified and shown to be both heat labile and susceptible to proteases (Godkin, et al., 1982). OvIFN-τ was originally called ovine trophoblast protein-one (oTP-1) because it was the primary secretory protein initially produced by trophectoderm of the sheep conceptus during the critical period of maternal recognition in sheep. Subsequent experiments have determined that OvIFN-τ is a pregnancy recognition hormone essential for establishment of the physiological response to pregnancy in ruminants, such as sheep and cows (Bazer and Johnson, 1991).

An IFN-τ cDNA obtained by probing a sheep blastocyst library with a synthetic oligonucleotide representing the N-terminal amino acid sequence (Imakawa, et al., 1987) has a predicted amino acid sequence that is 45–55% homologous with IFN-αs from human, mouse, rat and pig and 70% homologous with bovine IFN-αII, now referred to as IFN-Ω. Several cDNA sequences have been reported which may represent different isoforms (Stewart, et al., 1989; Klemann, et al., 1990; and Charlier, M., et al., 1991). All are approximately 1 kb with a 585 base open reading frame that codes for a 23 amino acid leader sequence and a 172 amino acid mature protein. The predicted structure of IFN-τ as a four helical bundle with the amino and carboxyl-termini in apposition further supports its classification as a type I IFN (Jarpe, et al., 1994).

TABLE 1

Overview of the Interferons

| Aspects | Type I | Type I | Type I | Type II |
|---|---|---|---|---|
| Types | α & ω | β | τ | γ |
| Produced by: | leukocyte | fibroblast | trophoblast | lymphocyte |
| Antiviral | + | + | + | + |
| Antiproliferative | + | + | + | + |
| Pregnancy Signaling | − | − | + | − |

While IFN-τ displays many of the activities classically associated with type I IFNs (see Table 1, above), considerable differences exist between it and the other type I IFNs. The most prominent difference is its role in pregnancy, detailed above. Also different is viral induction. All type I IFNs, except IFN-τ, are induced readily by virus and dsRNA (Roberts, et al., 1992). Induced IFN-α and IFN-β expression is transient, lasting approximately a few hours. In contrast, IFN-τ synthesis, once induced, is maintained over a period of days (Godkin, et al., 1982). On a per-cell basis, 300-fold more IFN-τ is produced than other type I IFNs (Cross and Roberts, 1991).

Other differences may exist in the regulatory regions of the IFN-τ gene. For example, transfection of the human trophoblast cell line JAR with the gene for bovine IFN-τ resulted in antiviral activity while transfection with the bovine IFN-Ω gene did not. This implies unique transacting factors involved in IFN-τ gene expression. Consistent with this is the observation that while the proximal promoter region (from 126 to the transcriptional start site) of IFN-τ is highly homologous to that of IFN-α and IFN-β; the region from −126 to −450 is not homologous and enhances only IFN-τ expression (Cross and Roberts, 1991). Thus, different regulatory factors appear to be involved in IFN-τ expression as compared with the other type I IFNs.

IFN-τ expression may also differ between species. For example, although IFN-τ expression is restricted to a particular stage (primarily days 13–21) of conceptus development in ruminants (Godkin, et al., 1982), preliminary studies suggest that the human form of IFN-τ is constitutively expressed throughout pregnancy (Whaley, et al., 1994).

A. Isolation of IFN-τ

OvIFN-τ protein may be isolated from conceptuses collected from pregnant sheep and cultured in vitro in a modified Minimum Essential Medium (MEM) as described by Godkin, et al., (1982) and Vallet, et al., (1987). The IFN-τ may be purified from the conceptus cultures by ion exchange chromatography and gel filtration. The homogeneity of isolated IFN-τ may be assessed by sodium dodecyl sulfate polyacrylamide gel electrophoresis (SDS-PAGE; Maniatis, et al., 1982; Ausubel, et al., 1988), and determination of protein concentration in purified IFN-τ samples may be performed using the bicinchoninic (BCA) assay (Pierce Chemical Co., Rockford, Ill.; Smith, et al., 1985).

B. Recombinant Production of IFN-τ

Recombinant IFN-τ protein may be produced from any selected IFN-τ polynucleotide fragment using a suitable expression system, such as bacterial or yeast cells. The isolation of IFN-τ nucleotide and polypeptide sequences is described in Bazer, et al. (1994). For example, Bazer, et al., describe the identification and isolation of a human IFN-τ gene.

To make an IFN-τ expression vector, an IFN-τ coding sequence (e.g, SEQ ID NOS: 1 or 3) is placed in an expression vector, e.g., a bacterial expression vector, and expressed according to standard methods. Examples of suitable vectors include lambda gt11 (Promega, Madison Wis.); pGEX (Smith, et al., 1985); pGEMEX (Promega); and pBS (Strategene, La Jolla Calif.) vectors. Other bacterial expression vectors containing suitable promoters, such as the T7 RNA polymerase promoter or the tac promoter, may also be used. Cloning of the OvIFN-τ synthetic polynucleotide into a modified pIN III omp-A expression vector is described in the Materials and Methods.

For the experiments described herein, the OvIFN-τ coding sequence present in SEQ ID NO: 3 was cloned into a vector, suitable for transformation of yeast cells, containing the methanol-regulated alcohol oxidase (AOX) promoter and a Pho1 signal sequence. The vector was used to transform $P.$ pastoris host cells and transformed cells were used to express the protein according to the manufacturer's instructions (Invitrogen, San Diego, Calif.).

Other yeast vectors suitable for expressing IFN-τ for use with methods of the present invention include 2 micron plasmid vectors (Ludwig, et al., 1993), yeast integrating plasmids (Ylps; e.g., Shaw, et al., 1988), YEP vectors (Shen, et al., 1986), yeast centromere plasmids (YCps; e.g.), and other vectors with regulatable expression (Hitzeman, et al., 1988; Rutter, et al., 1988; Oeda, et al., 1988). Preferably, the vectors include an expression cassette containing an effective yeast promoter, such as the MFα1 promoter (Bayne, et al., 1988, GADPH promoter (glyceraldehyde-3-phosphate-dehydrogenase; Wu, et al., 1991) or the galactose-inducible GAL 10 promoter (Ludwig, et al., 1993; Feher, et al., 1989; Shen, et al., 1986). The yeast transformation host is typically Saccharomyces cerevisiae, however, as illustrated above, other yeast suitable for transformation can be used as well (e.g., Schizosaccharomyces pombe, Pichia pastoris and the like).

Further, a DNA encoding an IFN-τ polypeptide can be cloned into any number of commercially available vectors to generate expression of the polypeptide in the appropriate host system. These systems include the above described bacterial and yeast expression systems as well as the following: baculovirus expression (Reilly, et al., 1992; Beames, et al., 1991; Clontech, Palo Alto Calif.); plant cell expression, transgenic plant expression, and expression in mammalian cells (Clontech, Palo Alto Calif.; Gibco-BRL, Gaithersburg Md.). The recombinant polypeptides can be expressed as fusion proteins or as native proteins. A number of features can be engineered into the expression vectors, such as leader sequences which promote the secretion of the expressed sequences into culture medium. The recombinantly produced polypeptides are typically isolated from lysed cells or culture media. Purification can be carried out by methods known in the art including salt fractionation, ion exchange chromatography, and affinity chromatography. Immunoaffinity chromatography can be employed, as described above, using antibodies generated based on the IFN-τ polypeptides.

In addition to recombinant methods, IFN-τ proteins or polypeptides can be isolated from selected cells by affinity-based methods, such as by using appropriate antibodies. Further, IFN-τ peptides (e.g. SEQ ID NOS: 2 or 4) may be chemically synthesized using methods known to those skilled in the art.

III. IFN-τ as a Treatment for HCV

Compositions and methods of the present invention may be used to therapeutically treat and thereby alleviate hepatitis caused by HCV. A person suffering from chronic hepatitis C infection may exhibit one or more of the following signs or symptoms: (a) elevated alanine aminotransferase (ALT), (b) positive test for anti-HCV antibodies, (c) presence of HCV as demonstrated by a positive test for HCV-RNA, (d) clinical stigmata of chronic liver disease, (e) hepatocellular damage, and/or (f) altered blood levels of 2',5'-oligoadenylate synthetase. Such criteria may not only be used to diagnose hepatitis C, but can be used to evaluate a patient's response to drug treatment.

Interferon causes synthesis of the enzyme 2',5'-oligoadenylate synthetase (OAS), which in turn, results in the degradation of viral mRNA (Houglum, 1983). OAS activates an RNase that cleaves cellular and viral RNAs, thereby inactivating viral replication (Kumar et al., 1988). OAS is considered responsible, at least in part, for the antiviral state established in cells and plays a role in the elimination of HCV (Pawlotsky, et al., 1995).

A. IFN Administered Orally and Intraperioneally Induce OAS

Figure 1:
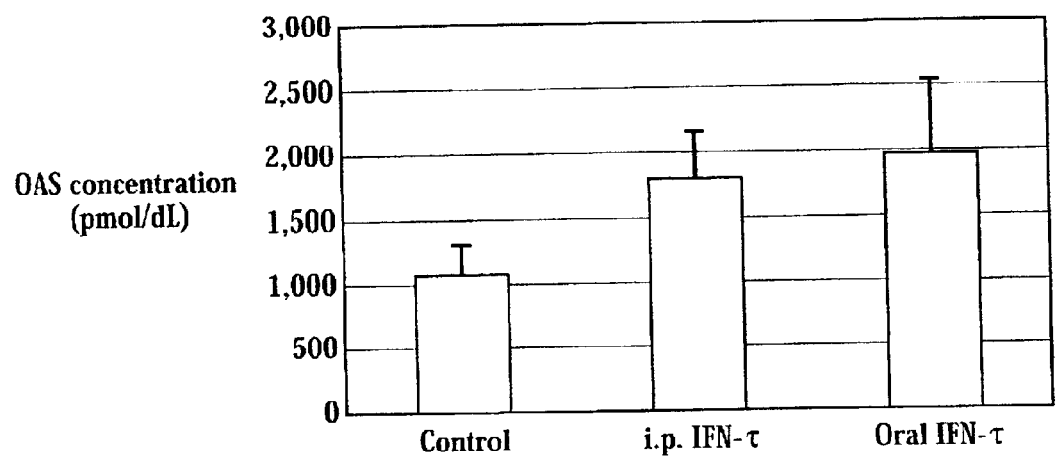
FIG. 1 shows OAS levels in mice whole blood following intraperitoneal (I.P.) or gastric administration (G.A.) of ovIFN-τ.

In experiments performed in support of the present invention and detailed in Examples 1 and 3, IFN-τ, administered orally, was tested for its ability to induce OAS. OvIFN-τ was administered either orally or intraperitoneally to mice or human patients. OAS activity in whole blood in mice was determined, and is shown in FIG. 1, 24 hours after IFN-τ administration. Several human patients had 2 to 12 fold increases in their OAS enzyme activity levels as shown in Tables 3–6.

When OvIFN-τ was administered orally or intraperitoneally in mice, an increase in the OAS activity in whole blood was observed. When the effect of orally administered OvIFN-τ and that of intraperitoneally administered OvIFN-τ in mice were compared, both administrations provided essentially the same whole blood OAS induction activity.

B. Orally Administered IFN-τ Induces OAS in a Dose-dependent Manner

Figure 2:
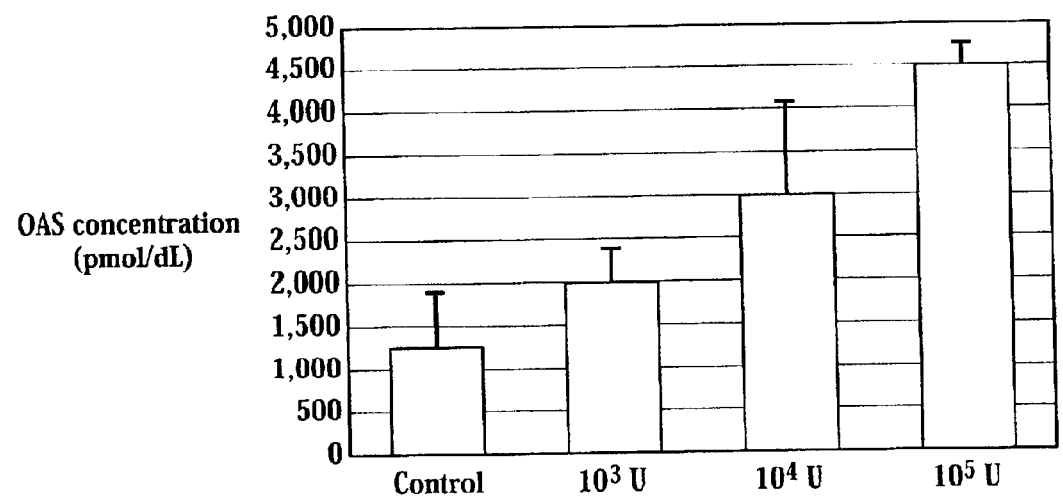
FIG. 2 shows dose-dependent induction of blood OAS by gastric administration (G.A.) of ovIFN-τ.
Figure 3:
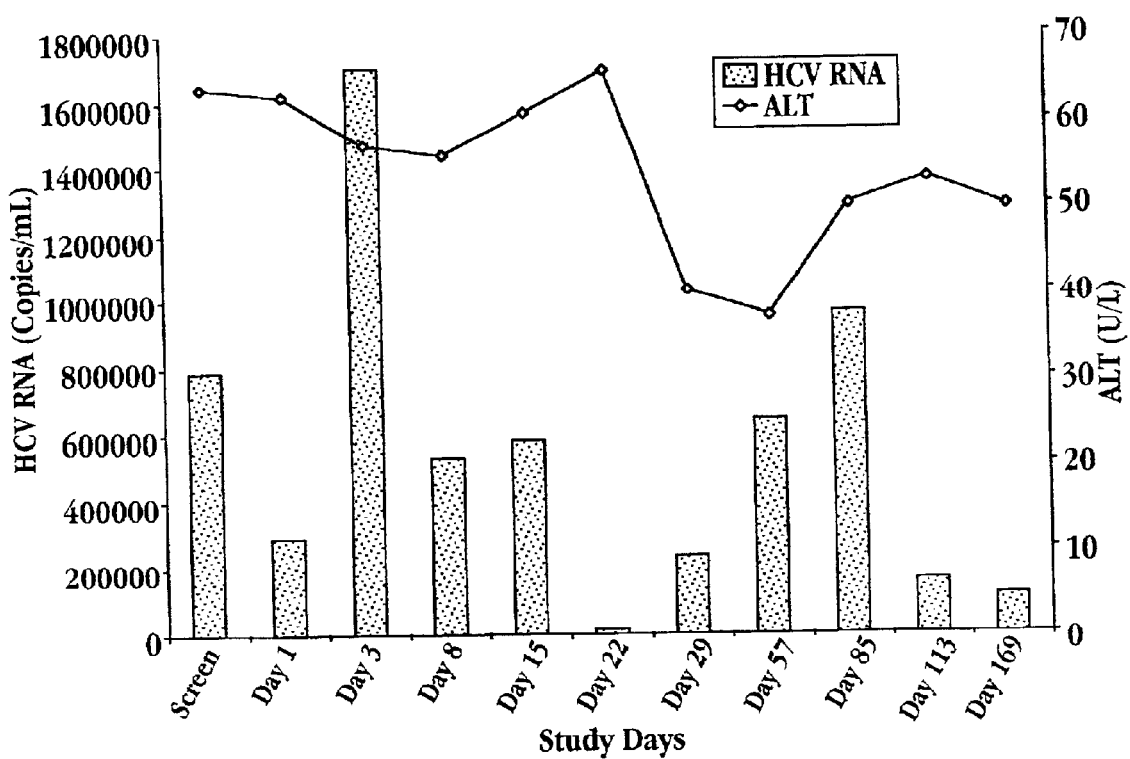
FIGS. 3–5 illustrate HCV RNA and ALT levels in three human patients following oral administration of $4.9 \times 10^8$ units/day ovIFN-τ.

In experiments performed in support of the present invention and detailed in Example 2, IFN-τ administered orally in mice, was tested for its ability to induce OAS in a dose-dependent manner. OvIFN-τ was orally administered in units of 0, $1\times10^3$, $1\times10^4$, $1\times10^5$ to an upper part of a mouse stomach. Twelve hours after oral administration, whole blood was taken from a mouse heart and an OAS activity of whole blood was determined. As shown in FIG. 2, the OAS activity in whole blood increased in a dose dependent manner.

Although it has already been established that IFN-τ is orally active (WO 96/28183), no exact determination has previously been made as to how IFN-τ was administered, or as to how IFN-τ is absorbed. In the present invention, IFN-τ was directly administered into the mouse stomach without any exposure to the tunica mucosa oris, conclusively esablishing that absorption through the stomach mucosal membrane effectively induces OAS activity. Direct absorption of IFN-τ from the stomach would diminish antibody formation against IFN-τ compared to IFN-τ absorbed through the oral mucosal membrane, particularly in the case of chronic administrations of IFN-τ.

In addition, the present invention describes the ability of ovine IFN-τ to increase 2',5'-oligoadenylate synthase activity in mice and humans. Prior to this work, only mouse IFN-τ had been known to be effective in mice.

IV. Administration of IFN-τ

A. Pharmaceutical Compositions

Therapeutic preparations or medicaments containing IFN-τ or related polypeptides or proteins can be formulated and manufactured according to known methods for preparing pharmaceutically useful compositions (medicaments). Formulations comprising interferons or interferon-like compounds have been previously described (e.g., Martin, 1976). In general., the IFN-τ-containing medicaments are formulated such that an effective amount of the IFN-τ is combined with a suitable carrier and/or excipient in order to facilitate effective administration of the composition. IFN-τ, or related polypeptides, may be administered to a patient in any pharmaceutically acceptable dosage form, including intravenous, intramuscular, intralesional., or subcutaneous injection. Specifically, compositions and methods used for other interferon compounds can be used for the delivery of these compounds.

In the case of compositions suitable for oral administration, tablets and capsules containing IFN-τ may be manufactured from IFN-τ (e.g., lyophilized IFN-τ protein) and, optionally, additives such as pharmaceutically acceptable carriers (e.g., lactose, corn starch, light silicic anhydride, microcrystalline cellulose, sucrose), binders (e.g., alpha-form starch, methylcellulose, carboxymethylcellulose, hydroxypropylcellulose, hydroxypropylmethylcellulose, polyvinylpyrrolidone), disintegrating agents (e.g., carboxymethylcellulose calcium, starch, low substituted hydroxy-propylcellulose), surfactants (e.g., Tween 80, polyoxyethylene-polyoxypropylene copolymer), antioxidants (e.g., L-cysteine, sodium sulfite, sodium ascorbate), lubricants (e.g., magnesium stearate, talc), and the like.

Further, IFN-τ polypeptides can be mixed with a solid, pulverulent or other carrier, for example lactose, saccharose, sorbitol, mannitol, starch, such as potato starch, corn starch, millopectine, cellulose derivative or gelatine, and may also include lubricants, such as magnesium or calcium stearate, or polyethylene glycol waxes compressed to the formation of tablets. By using several layers of the carrier or diluent, tablets operating with slow release can be prepared.

Liquid preparations for oral administration can be made in the form of elixirs, syrups or suspensions, for example solutions containing from about 0.1% to about 30% by weight of IFN-τ, sugar and a mixture of ethanol, water, glycerol, propylene, glycol and possibly other additives of a conventional nature.

B. Dosage

An orally active IFN-τ pharmaceutical composition is administered in a therapeutically effective amount to an individual in need of treatment. The dose may vary considerably and is dependent on factors such as the seriousness of the disorder, the age and the weight of the patient, other medications that the patient may be taking and the like. This amount or dosage is typically determined by the attending physician. The dosage will typically be between about $1 \times 10^5$ and $1 \times 10^{10}$ units/day, preferably between about $1 \times 10^8$ and $1.5 \times 10^9$ units/day. It will be appreciated that because of its lower toxicity, IFN-τ can be administered at higher doses than, for example, IFN-α.

Disorders requiring a steady elevated level of IFN-τ in plasma will benefit from oral administration as often as about every two to four hours or administration via injection about every 12–24 hours, while other disorders may be effectively treated by administering a therapeutically-effective dose at less frequent intervals, e.g., once every 48 hours. The rate of administration of individual doses is typically adjusted by an attending physician to enable administration of the lowest total dosage while alleviating the severity of the disease being treated.

Once improvement of a patient's condition has occurred, a maintenance dose is administered if necessary. Subsequently, the dosage or the frequency of administration, or both, may be reduced, as a function of the symptoms, to a level at which the improved condition is retained.

C. Combination Therapies

It will, of course, be understood that the compositions and methods of this invention may be used in combination with other therapies. For example, the composition of ovIFN-τ for the treatment of HCV in a HCV-infected patient can be combined with an anti-viral agent such as ribavirin.

D. Monitoring

Treatment of HCV by oral administration of ovIFN-τ is monitored by measuring the blood levels of 2',5'-oligoadenylate synthetase (OAS) prior to and following administration. The OAS levels can be monitored, for example, at 12, 24, and 48 hours after administration. If necessary, the dose of IFN-τ is adjusted until a measurable increase in blood OAS levels is observed, relative to the level observed prior to administration.

All patent and literature references cited in the present specification are hereby incorporated by reference in their entirety.

The following examples illustrate, but are not intended in any way to limit the invention.

Materials and Methods

A. Production of OvIFN-τ

In one embodiment, a synthetic OvIFN-τ gene was generated using standard molecular methods (Ausubel, et al., 1988) by ligating oligonucleotides containing contiguous portions of a DNA sequence encoding the OvIFN-τ amino acid sequence. The DNA sequence used may be either SEQ ID NO: 1 or 3 or the sequence as shown in Imakawa, et al., 1987. The resulting IFN-τ polynucleotide coding sequence may span position 16 through 531: a coding sequence of 172 amino acids.

In one embodiment, the full length synthetic gene StuI/SStI fragment (540 bp) may be cloned into a modified pIN III omp-A expression vector and transformed into a competent SB221 strain of *E. coli*. For expression of the IFN-τ protein, cells carrying the expression vector were grown in L-broth containing ampicillin to an OD (550 nm) of 0.1–1, induced with IPTG (isopropyl-1-thio-b-D-galactoside) for 3 hours and harvested by centrifugation. Soluble recombinant IFN-τ may be liberated from the cells by sonication or osmotic fractionation.

For expression in yeast, the IFN-τ gene may amplified using polymerase chain reaction (PCR; Mullis, 1987; Mullis, et al., 1987) with PCR primers containing StuI and SacI restriction sites at the 5' and 3' ends, respectively. The amplified fragments were digested with StuI and SacII and ligated into the SacII and SmaI sites of pBLUESCRIPT+ (KS), generating pBSY-IFNτ. Plasmid pBSY-IFNτ was digested with SacII and EcoRV and the fragment containing the synthetic IFN-τ gene was isolated. The yeast expression vector pBS24Ub (Ecker, et al., 1989) was digested with SalI. Blunt ends were generated using T4 DNA polymerase. The vector DNA was extracted with phenol and ethanol precipitated (Sambrook, et al., 1989). The recovered plasmid was digested with SacII, purified by agarose gel electrophoresis, and ligated to the SacII-EcoRV fragment isolated from pBSY-IFN-τ. The resulting recombinant plasmid was designated pBS24Ub-IFNτ.

The recombinant plasmid pBS24Ub-IFNτ was transformed into *E. coli*. Recombinant clones containing the IFN-τ insert were isolated and identified by restriction enzyme analysis. IFN-τ coding sequences were isolated from pBS24Ub-IFNτ and cloned into a *Pichia pastoris* vector containing the alcohol oxidase (AOX1) promoter (Invitrogen, San Diego, Calif.). The vector was then used to transform *Pichia pastors* GS115 His⁻ host cells and protein was expressed following the manufacturer's instructions. The protein was secreted into the medium and purified by successive DEAE-cellulose and hydroxyapatite chromatography to electrophoretic homogeneity as determined by SDS-PAGE and silver staining.

In one embodiment, the purified IFN-τ protein has a specific activity of about 0.29 to about $0.44 \times 10^8$ U/mg as measured by anti-viral activity on Madin-Darby bovine kidney (MDBK) cells. In another embodiment, the protein has a specific activity of about $4.9 \times 10^8$ U/mg as measured by the anti-viral activity bioassay.

EXAMPLE 1

Induction of OAS with Orally and Intraperitoneally Administered Ovine IFN-τ to Mice OvIFN-τ ($4.99 \times 10^8$ units/mg protein; Pepgen Corp., California or Biological Process Development Facility, Dept. of Food Science and Technology, University of NE-Lincoln, Lincoln, Nebr.; SEQ ID NO: 4) was dissolved in 10% maltose solution to prepare ovIFN-τ Solution. The use of OvIFN-τ (SEQ ID NO: 2) is also contemplated in the present invention. Two hundred microliters of ovIFN-τ solution was orally administered to ICR mice (average body weight approximately 30 g, 6 weeks of age, female) using a 20 gauge disposable oral sound (Fuchigami, Kyoto) to inject directly to an upper part of the stomach (gastric administration; GA.).

For intraperitoneal administration (I.P.), 100 microliters of ovIFN-τ solution was used. Sample injection to an upper part of a stomach was confirmed by administration of a dye. Twenty-four hours after the administration, the mouse was anesthetized with Nembutal. Blood was taken from a heart of the mouse and an OAS activity in whole blood was determined by 2–5A RIA Kit (Eiken Chemical., Tokyo; Shindo et al., 1989).

When the effect of orally administered $10^5$ units of ovIFN-τ (τ GA) and that of intraperitoneally administered $10^5$ units of OvIFN-τ (τ IP) were compared, both administrations provided essentially the same whole blood OAS induction activity. The results are shown in FIG. 1.

EXAMPLE 2

Dose-dependent Induction of OAS by Oral Administration of IFN-τ in Mice

Using the same procedure as Example 1, OvIFN-τ was orally administered in units of 0, $10^3$, $10^4$, or $10^5$ to an ICR mouse. Twelve hours after oral administration, whole blood was taken from a mouse heart and an OAS activity of whole blood was determined. As shown in FIG. 2, the OAS activity in whole blood increased in a dose dependent manner.

EXAMPLE 3

Reduced ALT, Reduced HCV Viral Titer, and Induction of OAS by Oral Administration of IFN-τ in Human Patients A. IFN-τ Preparation On day one, one bottle of Ov-IFN-τ (SEQ ID NO: 4) is removed from the refrigerator and the patient self-administers the proper volume of test material according to Table 2. Ov-IFN-τ (SEQ ID NO: 2) may also be prepared and administered in the same manner.

TABLE 2

Recombinant Ov-IFN-τ Patient Dose Administration

| Dose Group | Number of Patients | Ov-IFN-τ (mg/ml) | Volume (ml) per Dose (TID) | Total Daily Dose (ml) |
|---|---|---|---|---|
| I | 6 | 1.0 | 0.33 | 1.0 |
| II | 6 | 1.0 | 1.0 | 3.0 |
| III | 6 | 1.0 | 3.0 | 9.0 |
| IV | 6 | 1.0 | 5.0 | 15.0 |

B. Patient Dosing Instructions

The patient keeps all vials of test material and syringes in the refrigerator maintained at 2 to 8 degrees centigrade. Prior to the self-administration of medication, the patient remove one vial and one syringe from the refrigerator. The patient removes the cap from the tip of the syringe, places the tip of the syringe into the bottle of medication and withdraws the appropriate amount of drug into the syringe as instructed at the clinic on Day 1.

The patient places the tip of the syringe in the mouth and empties the contents of the syringe into the mouth by depressing the plunger. The patient then swallows the test material. The patient may then drink a glass of water. The patient notes on his/her diary card the date and time the dose of test material was administered.

The above steps are repeated three times per day at approximately eight-hour intervals: once in the morning, once at midday and once in the evening.

C. Results

The results of the human clinical trails in patients with HCV infections are shown in Table 3–10 below, and graphically in FIGS. 3–7. An increase in OAS levels, and a decrease in both ALT and viral titer levels following oral ovine IFN-τ administration can be seen below.

TABLE 3

Human Clinical Trial Data - BB-IND9222 Dose Cohort I

| PEPGEN OS NUMBER | Patient Initials/# | Timept. | Date Collected | HCV RT-PCR | ALT (IU/L) | 2-5A (SERUM) pmol/dl 2-5A | 2-5 (PBMC) pmol/5 × $10^6$ PBMC/ml |
|---|---|---|---|---|---|---|---|
| 180 | PAB/001 | Screen | Nov. 17, 2000 | 790,000 | 64 | 12.46 | — |
| 181 | PAB/001 | Day 1 | Dec. 1, 2000 | 290,000 | 63 | 10.00 | — |
| 337 | PAB/001 | day 2/ | Dec. 2, 2000 | — | — | 10.00 | — |

TABLE 3-continued

Human Clinical Trial Data - BB-IND9222 Dose Cohort I

| PEPGEN OS NUMBER | Patient Initials/# | Timept. | Date Collected | HCV RT-PCR | ALT (IU/L) | 2-5A (SERUM) pmol/dl 2-5A | 2-5 (PBMC) pmol/5 × 10$^6$ PBMC/ml |
|---|---|---|---|---|---|---|---|
| 182 | PAB/001 | 24 hr. | Dec. 3, 2000 | 1,700,000 | 57 | 5.00 | — |
| 183 | PAB/001 | Day 3 | Dec. 8, 2000 | 530,000 | 56 | 5.00 | — |
| 184 | PAB/001 | Day 8 | Dec. 15, 2000 | 580,000 | 61 | 0.00 | — |
| 185 | PAB/001 | Day 15 | Dec. 22, 2000 | 13,000 | 66 | 2.50 | — |
| 186 | PAB/001 | Day 22 | Dec. 29, 2000 | 230,000 | 40 | 10.00 | — |
| 187 | PAB/001 | Day 29 | Jan. 12, 2001 | — | 42 | 7.50 | — |
| 188 | PAB/001 | Day 43 | Jan. 26, 2001 | 640,000 | 37 | 16.67 | — |
| 189 | PAB/001 | Day 57 | Feb. 9, 2001 | — | — | 12/46 | — |
| 190 | PAB/001 | Day 71 | Feb. 23, 2001 | 960,000 | 50 | 13.86 | — |
| 191 | PAB/001 | Day 85 | Mar. 23, 2001 | 160,000 | 53 | 0.00 | — |
| 192 | PAB/001 | Day 113 |  |  |  |  | — |
| 193 | MSM/002 | Day 169 | Nov. 27, 2000 | 4,600,000 | 258 | 11.05 | — |
| 194 | MSM/002 | Screen | Dec. 11, 2000 | 5,100,000 | 164 | 16.67 | — |
| 337 | MSM/002 | Day 1 | Dec. 12, 2000 | — | — | 10.00 | — |
| 195 | MSM/002 | Day 2/ 24 hr. | Dec. 13, 2000 | 6,300,000 | 154 | 29.30 | — |
| 196 | MSM/002 | Day 3 | Dec. 18, 2000 | 5,100,000 | 133 | 33.08 | — |
| 197 | MSM/002 | Day 8 | Dec. 26, 2000 | 9,100,000 | 100 | 54.62 | — |
| 198 | MSM/002 | Day 15 | Jan. 2, 2001 | — | 103 | 51.54 | — |
| 199 | MSM/002 | Day 22 | Jan. 8, 2001 | 8,600,000 | 91 | 28.60 | — |
| 200 | MSM/002 | Day 29 | Jan. 23, 2001 | — | 86 | 12.46 | — |
| 201 | MSM/002 | Day 43 | Feb. 7, 2001 | 3,400,000 | 82 | 18.77 | — |
| 202 | MSM/002 | Day 57 | Feb. 20, 2001 | — | — | 36.15 | — |
| 203 | MSM/002 | Day 71 | Mar. 2, 2001 | 3,700,000 | 49 | 26.14 | — |
| 204 | MSM/002 | Day 85 | Apr. 3, 2001 | 3,800,000 | 64 | 42.31 | — |
| 205 | MSM/002 | Day 113 |  |  |  |  | — |
| 206 | DMA/003 | Day 169 | Dec. 1, 2000 | 780,000 | 115 | 28.60 | — |
| 207 | DMA/003 | Screen | Dec. 12, 2000 | 990,000 | 115 | 26.14 | — |
| 208 | DMA/003 | Day 1 | Dec. 14, 2000 | 660,000 | 121 | 30.00 | — |
| 209 | DMA/003 | Day 3 | Dec. 19, 2000 | 920,000 | 105 | 36.15 | — |
| 210 | DMA/003 | Day 8 | Dec. 26, 2000 | 580,000 | 107 | 26.14 | — |
| 211 | DMA/003 | Day 15 | Jan. 2, 2001 | — | 105 | 24.74 | — |
| 212 | DMA/003 | Day 22 | Jan. 9, 2001 | 170,000 | 97 | 27.54 | — |
| 213 | DMA/003 | Day 29 | Jan. 22, 2001 | — | 85 | 23.33 | — |
| 214 | DMA/003 | Day 43 | Feb. 5, 2001 | 650,000 | 74 | 59.23 | — |
| 215 | DMA/003 | Day 57 | Feb. 20, 2001 | — | — | 36.15 | — |
| 216 | DMA/003 | Day 71 | Mar. 5, 2001 | 11,000 | 49 | 16.00 | — |
| 217 | DMA/003 | Day 85 | Mar. 27, 2001 | 880,000 | 45 | 0.00 | — |
| 217 | DMA/003 | Day 107 | Apr. 4, 2000 | 50,000 | 55 | 20.24 | — |
|  | DMA/003 | Day 115 |  | 460,000 | 47 |  |  |

TABLE 4

HEPC CLINICAL TRIALS BB-IND9222 DOSE COHORT I

| PEPGEN OS NUMBER | Patient Initials/# | Timept. | Date Collected | HCV RT-PCR | ALT (IU/L) | 2-5A (SERUM) pmol/dl 2-5A | 2-5 (PBMC) pmol/5 × 10$^6$ PBMC/ml |
|---|---|---|---|---|---|---|---|
| 219 | LER/004 | Screen | Dec. 12, 2000 | 6,100,000 | 118 | 33.95 | — |
| 220 | LER/004 | Day 1 | Dec. 20, 2000 | 6,000,000 | 108 | 33.95 | — |
| 221 | LER/004 | Day 3 | Dec. 22, 2000 | 11,000,000 | 120 | 53.68 | — |
| 222 | LER/004 | Day 8 | Dec. 27, 2000 | 1,900,000 | 109 | 29.51 | — |
| 223 | LER/004 | Day 15 | Jan. 3, 2001 | 3,400,000 | 120 | 41.84 | — |
| 224 | LER/004 | Day 22 | Jan. 10, 2001 | — | 94 | 34.74 | — |
| 225 | LER/004 | Day 29 | Jan. 17, 2001 | 640,000 | 109 | 43.42 | — |
| 226 | LER/004 | Day 43 | Jan. 30, 2001 | — | 99 | 49.74 | — |
| 227 | LER/004 | Day 57 | Feb. 13, 2001 | 4,400,000 | 106 | 37.89 | — |
| 228 | LER/004 | Day 71 | Feb. 27, 2001 | — | — | 81.00 | — |
| 229 | LER/004 | Day 85 | Mar. 14, 2001 | 3,900,000 | 67 | 3.20 | — |
| 230 | LER/004 | Day 113 |  | 3,200,000 | 107 |  | — |
| 231 | LER/004 | Day 169 |  |  |  |  | — |
| 232 | Z-I/005 | Screen | Dec. 20, 2000 | 3,400,000 | 151 | 43.42 | — |
| 233 | Z-I/005 | Day 1 | Jan. 8, 2001 | 4,600,000 | 134 | 43.42 | — |
| 338 | Z-I/005 | Day 2/ 24 hr. | Jan. 2, 2001 | — | 144 | 45.00 | — |
| 234 | Z-I/005 | Day 3 | Jan. 10, 2001 | 1,400,000 | 109 | 46.58 | — |
| 235 | Z-I/005 | Day 8 | Jan. 15, 2001 | 4,000,000 | 94 | 12/93 | — |
| 236 | Z-I/005 | Day 15 | Jan. 22, 2001 | 1,100,000 | 107 | 48.95 |  |

TABLE 4-continued

HEPC CLINICAL TRIALS BB-IND9222 DOSE COHORT I

| PEPGEN OS NUMBER | Patient Initials/# | Timept. | Date Collected | HCV RT-PCR | ALT (IU/L) | 2-5A (SERUM) pmol/dl 2-5A | 2-5 (PBMC) pmol/5 × 10⁶ PBMC/ml |
|---|---|---|---|---|---|---|---|
| 237 | Z-I/005 | Day 22 | Jan. 31, 2001 | — | 107 | 47.37 | — |
| 238 | Z-I/005 | Day 29 | Feb. 7, 2001 | 2,200,000 | 144 | 74.82 | — |
| 239 | Z-I/005 | Day 43 | Feb. 19, 2001 | — | 111 | 26.10 | — |
| 240 | Z-I/005 | Day 57 | Mar. 5, 2001 | 4,400,000 | 122 | 43.42 | — |
| 241 | Z-I/005 | Day 71 | Mar. 19, 2001 | — | — | 10.00 | — |
| 242 | Z-I/005 | Day 85 | Apr. 4, 2001 | 1,100,000 | 122 | 17.80 | — |
| 243 | Z-I/005 | Day 113 | | 3,200,000 | 132 | | — |
| 244 | Z-I/005 | Day 169 | | | | | — |
| 245 | JRJ/006 | Screen | Jan. 5, 2001 | 21,000,000 | 111 | 52.11 | — |
| 246 | JRJ/006 | Day 1 | Jan. 10, 2001 | 8,500,000 | 104 | 21.90 | — |
| 247 | JRJ/006 | Day 3 | Jan. 12, 2001 | 6,000,000 | 98 | 26.53 | — |
| 248 | JRJ/006 | Day 8 | Jan. 17, 2001 | 950,000 | 124 | 24.21 | — |
| 249 | JRJ/006 | Day 15 | Jan. 24, 2001 | 3,700,000 | 118 | 19.09 | — |
| 250 | JRJ/006 | Day 22 | Jan. 30, 2001 | — | 109 | 22.07 | — |
| 251 | JRJ/006 | Day 29 | Feb. 7, 2001 | 3,300,000 | 93 | 19.75 | — |
| 252 | JRJ/006 | Day 43 | Feb. 22, 2001 | — | 122 | 24.88 | — |
| 253 | JRJ/006 | Day 57 | Mar. 7, 2001 | 7,000,000 | 78 | 35.62 | — |
| 254 | JRJ/006 | Day 71 | Mar. 21, 2001 | — | — | 52.92 | — |
| 255 | JRJ/006 | Day 85 | Apr. 4, 2001 | 5,000,000 | 88 | 42.92 | — |
| 256 | JRJ/006 | Day 113 | | >5,000,000 | 109 | | — |
| 257 | JRJ/006 | Day 169 | | | | | — |

TABLE 5

HEPC CLINICAL TRIALS BB-IND9222 DOSE COHORT II

| PEPGEN OS NUMBER | Patient Initials/# | Timept. | Date Collected | HCV RT-PCR | ALT (IU/L) | 2-5A (SERUM) pmol/dl 2-5A | 2-5 (PBMC) pmol/5 × 10⁶ PBMC/ml |
|---|---|---|---|---|---|---|---|
| | AMC/007 | Screen | Feb. 2, 2001 | 1,700,000 | 44 | 11.20 | — |
| | AMC/007 | Day 1 | Feb. 20, 2001 | 1,300,000 | 48 | 18.40 | — |
| | AMC/007 | Day 3 | Feb. 22, 2001 | 810,000 | 44 | 27.60 | — |
| | AMC/007 | Day 8 | Feb. 27, 2001 | 630,000 | 50 | 42.40 | — |
| | AMC/007 | Day 15 | Mar. 6, 2001 | 290,000 | 54 | 50.67 | — |
| | AMC/007 | Day 22 | Mar. 13, 2001 | — | 53 | 94.50 | — |
| | AMC/007 | Day 29 | Mar. 20, 2001 | 410,000 | 36 | 120.00 | — |
| | AMC/007 | Day 43 | Apr. 3, 2001 | — | 29 | 81.33 | — |
| | AMC/007 | Day 57 | Apr. 17, 2001 | 930,000 | 36 | 55.33 | — |
| | AMC/007 | Day 71 | May, 1, 2001 | — | — | 51.33 | — |
| | AMC/007 | Day 85 | May, 15, 2001 | | | | — |
| | AMC/007 | Day 113 | Jun. 12, 2001 | | | | — |
| | AMC/007 | Day 169 | Aug. 7, 2001 | | | | — |
| | ALW/008 | Screen | Feb. 2, 2001 | 30,000,000 | 47 | 53.33 | — |
| | ALW/008 | Day 1 | Feb. 20, 2001 | 3,000,000 | 38 | 10.00 | — |
| | ALW/008 | Day 3 | Feb. 22, 2001 | 3,200,000 | 42 | 42.00 | — |
| | ALW/008 | Day 8 | Feb. 27, 2001 | 5,400,000 | 31 | 14.40 | — |
| | ALW/008 | Day 15 | Mar. 6, 2001 | 17,000,000 | 29 | 10.00 | — |
| | ALW/008 | Day 22 | Mar. 13, 2001 | — | 27 | 10.40 | — |
| | ALW/008 | Day 29 | Mar. 20, 2001 | 11,000,000 | 25 | 10.00 | — |
| | ALW/008 | Day 43 | Apr. 3, 2001 | — | 40 | 14.40 | — |
| | ALW/008 | Day 57 | Apr. 17, 2001 | 18,000,000 | 31 | 12.80 | — |
| | ALW/008 | Day 71 | May 1, 2001 | — | — | 16.40 | — |
| | ALW/008 | Day 85 | May 15, 2001 | | | | — |
| | ALW/008 | Day 113 | Jun. 12, 2001 | | | | — |
| | ALW/008 | Day 169 | Aug. 7, 2001 | | | | — |
| | DBF/012 | Screen | | 5,300,000 | 84 | 28.80 | — |
| | DBF/012 | Day 1 | | 9,300,000 | 77 | 26.00 | — |
| | DBF/012 | Day 3 | | 9,400,000 | 71 | 10.00 | — |
| | DBF/012 | Day 8 | | 7,900,000 | 86 | 53.33 | — |
| | DBF/012 | Day 15 | | 9,100,000 | 67 | 108.00 | — |
| | DBF/012 | Day 22 | | — | 64 | 42.67 | — |
| | DBF/012 | Day 29 | | 9,900,000 | 58 | 52.00 | — |
| | DBF/012 | Day 43 | | — | 61 | 58.00 | — |
| | DBF/012 | Day 57 | | 15,000,000 | 70 | 61.33 | — |
| | DBF/012 | Day 71 | | — | — | 168.00 | — |
| | DBF/012 | Day 85 | | | | | — |
| | DBF/012 | Day 113 | | | | | — |
| | DBF/012 | Day 169 | | | | | — |

TABLE 6

HEPC CLINICAL TRIALS BB-IND9222 DOSE COHORT II

| PEPGEN OS NUMBER | Patient Initials/# | Timept. | Date Collected | HCV RT-PCR | ALT (IU/L) | 2-5A (SERUM) pmol/dl 2-5A | 2-5 (PBMC) pmol/5 × 10$^6$ PBMC/ml |
|---|---|---|---|---|---|---|---|
| | VCC/009 | Screen | Feb. 2, 2001 | 5,100,000 | 113 | 17.20 | — |
| | VCC/009 | Day 1 | Feb. 21, 2001 | 4,300,000 | 128 | 58.67 | 286.88 |
| | VCC/009 | Day 2/ 24 hr. | Feb. 22, 2001 | — | — | 10.00 | — |
| | VCC/009 | Day 3 | Feb. 23, 2001 | 3,500,000 | 126 | 18.40 | 218.57 |
| | VCC/009 | Day 8 | Feb. 28, 2001 | 1,600,000 | 130 | 24.80 | — |
| | VCC/009 | Day 15 | Mar. 7, 2001 | 2,200,000 | 118 | 25.20 | 624.38 |
| | VCC/009 | Day 22 | Mar. 14, 2001 | — | 99 | 18.00 | — |
| | VCC/009 | Day 29 | Mar. 21, 2001 | 1,500,000 | 93 | 30.67 | 1261.43 |
| | VCC/009 | Day 43 | Apr. 5, 2001 | — | 72 | 15.20 | — |
| | VCC/009 | Day 57 | Apr. 18, 2001 | 2,700,000 | 62 | 10.00 | — |
| | VCC/009 | Day 71 | May 2, 2001 | — | — | 18.40 | — |
| | VCC/009 | Day 85 | May 16, 2001 | | | — | — |
| | VCC/009 | Day 113 | Jun. 13, 2001 | | | | — |
| | VCC/009 | Day 169 | Aug. 8, 2001 | | | | — |
| | HCM/010 | Screen | Feb. 2, 2001 | 3,00,000 | 60 | 28.84 | — |
| | HCM/010 | Day 1 | Feb. 21, 2001 | 5,000,000 | 47 | 12.31 | 998.1 |
| | HCM/010 | Day 2/ 24 hr. | Feb. 22/2001 | — | — | — | — |
| | HCM/010 | Day 3 | Feb. 23, 2001 | 5,100,000 | 52 | 22.56 | 1336.67 |
| | HCM/010 | Day 8 | Feb. 28, 2001 | 5,100,000 | 50 | 18.6 | — |
| | HCM/010 | Day 15 | Mar. 7, 2001 | 5,300,000 | 49 | 30 | 1336.67 |
| | HCM/010 | Day 22 | Mar. 14, 2001 | — | 49 | 47.08 | — |
| | HCM/010 | Day 29 | Mar. 21, 2001 | 3,000,000 | 57 | 50 | 1524.76 |
| | HCM/010 | Day 43 | Apr. 4, 2001 | — | 45 | 246 | — |
| | HCM/010 | Day 57 | Apr. 18, 2001 | 4,300,000 | 59 | 16.67 | — |
| | HCM/010 | Day 71 | May 2, 2001 | — | — | 15.26 | — |
| | HCM/010 | Day 85 | May 16, 2001 | | | | — |
| | HCM/010 | Day 113 | Jun. 13, 2001 | | | | — |
| | HCM/010 | Day 169 | Aug. 8, 2001 | | | | |
| | CLR/011 | Screen | Feb. 5, 2001 | 12,000,000 | 58 | 10.00 | — |
| | CLR/011 | Day 1 | Feb. 21, 2001 | 19,000,000 | 66 | 30.00 | 960.48 |
| | CLR/011 | Day 3 | Feb. 23, 2001 | 28,000,000 | 55 | 11.05 | 922.86 |
| | CLR/011 | Day 8 | Feb. 28, 2001 | >5,000,000 | 55 | 12.46 | — |
| | CLR/011 | Day 15 | Mar. 7, 2001 | 23,000,000 | 63 | 12.46 | 1035.71 |
| | CLR/011 | Day 22 | Mar. 14, 2001 | — | 65 | 19.82 | — |
| | CLR/011 | Day 29 | Mar. 21, 2001 | 13,000,000 | 58 | 10.00 | 998.1 |
| | CLR/011 | Day 43 | Apr. 4, 2001 | — | 63 | 36.00 | — |
| | CLR/011 | Day 57 | Apr. 18, 2001 | 18,000,000 | 61 | 20.80 | — |
| | CLR/011 | Day 71 | May 2, 2001 | — | — | 10.00 | — |
| | CLR/011 | Day 85 | May 16, 2001 | | | | — |
| | CLR/011 | Day 113 | Jun. 13, 2001 | | | | — |
| | CLR/011 | Day 169 | Aug. 8, 2001 | | | | — |

TABLE 7

Dose Group 1 (0.33 mg TID) - 24 Hour Serum Collection PCR Assays (HCV RNA)

| Patient ID | Screen | Day 1 | Day 3 | Day 8 | Day 15 | Day 22 | Day 29 | Day 57 | Day 85 | Day 113 | Day 169 |
|---|---|---|---|---|---|---|---|---|---|---|---|
| 001 PAB | 790,000 | 290,000 | 1,700,000 | 530,000 | 580,000 | 13,000[1] | 230,000 | 640,000 | 960,000 | 160,000 | 110,000 |
| 002 MSM | 4,600,000 | 5,100,000 | 6,300,000 | 5,100,000 | 9,100,000 | | 8,600,000 | 3,400,000 | 3,700,000 | 3,800,000 | 1,900,000 |
| 003 DMA | 780,000 | 990,000 | 660,000 | 920,000 | 580,000 | | 170,000 | 650,000 | 11,000 | 880,000[2] 50,000[3] 460,000[4] | 340,000[5] |
| 004 LER | 6,100,000 | 6,000,000 | 11,000,000 | 1,900,000 | 3,400,000 | | 640,000 | 4,400,000 | 3,900,000 | 3,200,000 | 3,800,000 |
| 005 Z-I | 3,400,000 | 4,600,000 | 1,400,000 | 4,000,000 | 1,100,000 | | 2,200,000 | 4,400,000 | 1,100,000 | 3,200,000 | 1,300,000 |
| 006 JRJ | 21,000,000 | 8,500,000 | 6,000,000 | 950,000 | 3,700,000 | | 3,300,000 | 7,000,000 | 5,000,000 | 5,100,000 | >5,000,000 |

[1]PCR Assay not scheduled for Day 22
[2]Day 1 of Retreat
[3]Day 8 of Retreat
[4]Day 29 of Retreat
[5]Day 164 of Retreat

TABLE 8

ALT Values (IU/L) - Dose Group 1

| Patient ID | Screen | Day 1 | Day 3 | Day 8 | Day 15 | Day 22 | Day 29 | Day 43 | Day 57 | Day 85 | Day 113 | Day 169 |
|---|---|---|---|---|---|---|---|---|---|---|---|---|
| 001 PAB | 64 | 63 | 57 | 56 | 61 | 66 | 40* | 42* | 37* | 50 | 53 | 50 |
| 002 MSM | 258 | 164 | 154 | 133 | 100 | 103 | 91 | 86 | 82 | 49 | 64 | 61 |
| 003 DMA | 115 | 115 | 121 | 105 | 107 | 105 | 97 | 85 | 74 | 49 | 45 | 51 |
| 004 LER | 118 | 108 | 120 | 109 | 120 | 94 | 109 | 99 | 106 | 67 | 107 | 120 |
| 005 Z-I | 151 | 134 | 144 | 109 | 94 | 107 | 107 | 144 | 111 | 122 | 132 | |
| 006 JRJ | 111 | 104 | 98 | 124 | 118 | 109 | 93 | 122 | 78 | 88 | 109 | |
| Mean | 116.71 | 98.43 | 99.57 | 92 | 87.86 | 86.57 | 82.83 | 89.33 | 75.17 | 72.86 | 89 | 64.43 |
| Std | | | | | | | | | | | | |

[1]Normal ALT (range = 1–45)
[2]Day 1 of Retreat.
[3]Day 8 of Retreat.
[4]Day 29 of Retreat.
[5]Day 164 of Retreat
[6]Day 192 of Retreat

TABLE 9

Dose Group 2 (1.0 mg TID) - 24 Hour Serum Collection PCR Assays (HCV RNA)

| Patient ID | Screen | Day 1 | Day 3 | Day 8 | Day 15 | Day 29 | Day 57 | Day 85 | Day 113 | Day 169 |
|---|---|---|---|---|---|---|---|---|---|---|
| 007 AMC | 1,700,000 | 1,300,000 | 810,000 | 630,000 | 290,000 | 410,000 | 930,000 | 900,000 | 310,000 | |
| 008 ALW | 30,000,000 | 3,000,000 | 3,200,000 | 5,400,000 | 17,000,000 | 11,000,000 | 18,000,000 | 7,700,000 | 11,000,000 | |
| 009 VCC | 5,100,000 | 4,300,000 | 3,500,000 | 1,600,000 | 2,200,000 | 1,500,000 | 2,700,000 | 1,700,000 | 670,000 | |
| 010 HMC | 3,000,000 | 5,000,000 | 5,100,000 | 5,100,000 | 5,300,000 | 3,000,000 | 4,300,000 | 3,100,000 | 4,400,000 | |
| 011 CLR | 12,000,000 | 19,000,000 | 28,000,000 | >5,000,000 | 23,000,000 | 13,000,000 | 18,000,000 | 9,400,000 | 8,200,000 | |
| 012 DBF | 5,300,000 | 9,300,000 | 9,400,000 | 7,900,000 | 9,100,000 | 9,900,000 | 15,000,000 | 9,500,000 | 16,000,000 | |

TABLE 10

ALT Values (IU/L) - Dose Group 2

| Patient ID | Screen | Day 1 | Day 3 | Day 8 | Day 15 | Day 22 | Day 29 | Day 43 | Day 57 | Day 85 | Day 113 | Day 169 |
|---|---|---|---|---|---|---|---|---|---|---|---|---|
| 007 AMC | 44** | 48 | 44 | 50 | 54 | 53 | 36* | 29* | 36* | 37* | 49 | |
| 008 ALW | 47 | 38* | 42* | 31* | 29* | 27* | 25* | 40* | 31* | 31* | 25* | |
| 009 VCC | 113 | 128 | 126 | 130 | 118 | 99 | 93 | 72 | 62 | 38* | 34* | |
| 010 HMC | 60 | 47 | 52 | 50 | 49 | 49 | 57 | 45 | 59 | 51 | 58 | |
| 011 CLR | 58 | 66 | 55 | 55 | 63 | 65 | 58 | 63 | 61 | 60 | 61 | |
| 012 DBF | 84 | 77 | 71 | 86 | 67 | 64 | 58 | 61 | 70 | 89 | 92 | |

*Normal ALT Value (range = 1–45)
**Normal ALT Value for female 67 years of age (4–40)

---

It is claimed:

1. A method for decreasing the alanine aminotransferase (ALT) blood level in a human subject infected with hepatitis C virus (HCV), comprising orally administering interferon-tau to the subject at a daily dosage between $2 \times 10^8 - 10^{10}$ Units, said dosage effective to decrease bloodstream levels of ALT relative to bloodstream levels of ALT prior to treatment.

2. The method of claim 1, wherein said orally administering comprises orally administering interferon-tau formulated to avoid absorption through the *tunica mucosa oris*.

3. The method of claim 2, wherein said orally administering comprises orally administering interferon-tau contained in an oral-delivery vehicle effective to release the interferon-tau in active form in the digestive tract.

4. The method of claim 2, wherein said orally administering comprises orally administering interferon-tau contained in an oral-delivery vehicle effective to release interferon-tau in the stomach or intestines.

5. The method of claim 1, wherein said orally administering comprises orally administering interferon-tau at a dose greater than $4 \times 10^8$ Units per day.

6. The method of claim 1, further comprising administering a second anti-viral agent to the subject.

7. The method of claim 1, further comprising measuring the blood level of ALT in the subject prior to orally administering interferon-tau.

8. The method of claim 1, further comprising measuring the blood level of ALT in the subject after orally administering interferon-tau.

9. The method of claim 8, further comprising adjusting the dose of interferon-tau and continuing to administer at said adjusted dose.

* * * * *

SEQUENCE LISTING

<160> NUMBER OF SEQ ID NOS: 4

<210> SEQ ID NO 1
<211> LENGTH: 516
<212> TYPE: DNA
<213> ORGANISM: Ovis Aries

<400> SEQUENCE: 1

```
tgctacctgt cgcgaaaact gatgctggac gctcgagaaa atttaaaact gctggaccgt      60
atgaatcgat tgtctccgca cagctgcctg caagaccgga aagacttcgg tctgccgcag     120
gaaatggttg aaggtgacca actgcaaaaa gaccaagctt tcccggtact gtatgaaatg     180
ctgcagcagt cttttcaacct gttctacact gaacattctt cggccgcttg ggacactact     240
cttctagaac aactgcgcac tggtctgcaa cagcaactgg accatctgga cacttgcgct     300
ggccaggtta tgggtgaaga agactctgaa ctgggtaaca tggatccgat cgttactgtt     360
```

```
aaaaaatatt tccagggtat ctacgactac ctgcaggaaa aaggttactc tgactgcgct        420
tgggaaatcg tacgcgttga atgatgcgg gccctgactg tgtcgactac tctgcaaaaa         480
cggttaacta aaatgggtgg tgacctgaat tctccg                                   516
```

```
<210> SEQ ID NO 2
<211> LENGTH: 172
<212> TYPE: PRT
<213> ORGANISM: Ovis Aries

<400> SEQUENCE: 2
```

Cys Tyr Leu Ser Arg Lys Leu Met Leu Asp Ala Arg Glu Asn Leu Lys
1               5                   10                  15

Leu Leu Asp Arg Met Asn Arg Leu Ser Pro His Ser Cys Leu Gln Asp
            20                  25                  30

Arg Lys Asp Phe Gly Leu Pro Gln Glu Met Val Glu Gly Asp Gln Leu
        35                  40                  45

Gln Lys Asp Gln Ala Phe Pro Val Leu Tyr Glu Met Leu Gln Gln Ser
    50                  55                  60

Phe Asn Leu Phe Tyr Thr Glu His Ser Ser Ala Ala Trp Asp Thr Thr
65                  70                  75                  80

Leu Leu Glu Gln Leu Cys Thr Gly Leu Gln Gln Gln Leu Asp His Leu
                85                  90                  95

Asp Thr Cys Arg Gly Gln Val Met Gly Glu Glu Asp Ser Glu Leu Gly
            100                 105                 110

Asn Met Asp Pro Ile Val Thr Val Lys Lys Tyr Phe Gln Gly Ile Tyr
        115                 120                 125

Asp Tyr Leu Gln Glu Lys Gly Tyr Ser Asp Cys Ala Trp Glu Ile Val
    130                 135                 140

Arg Val Glu Met Met Arg Ala Leu Thr Val Ser Thr Thr Leu Gln Lys
145                 150                 155                 160

Arg Leu Thr Lys Met Gly Gly Asp Leu Asn Ser Pro
                165                 170

```
<210> SEQ ID NO 3
<211> LENGTH: 519
<212> TYPE: DNA
<213> ORGANISM: Artificial Sequence
<220> FEATURE:
<223> OTHER INFORMATION: recombinant IFNtau based on Ovis aries sequence

<400> SEQUENCE: 3
tgctacctgt cggagcgact gatgctggac gctcgagaaa atttaaaact gctggaccgt        60
atgaatcgat tgtctccgca cagctgcctg caagaccgga aagacttcgg tctgccgcag        120
gaaatggttg aaggtgacca actgcaaaaa gaccaagctt tcccggtact gtatgaaatg        180
ctgcagcagt ctttcaacct gttctacact gaacattctt cggccgcttg ggacactact        240
cttctagaac aactgtgcac tggtctgcaa cagcaactgg accatctgga cacttgccgt        300
ggccaagtta tgggtgaaga agactctgaa ctgggtaaca tggatccgat cgttactgtt        360
aaaaaatatt tccagggtat ctacgactac ctgcaggaaa aaggttactc tgactgcgct        420
tgggaaatcg tacgcgttga atgatgcgg gccctgactg tgtcgactac tctgcaaaaa         480
cggttaacta aaatgggtgg tgacctgaat tctccgtaa                                519
```

```
<210> SEQ ID NO 4
<211> LENGTH: 172
```

```
<212> TYPE: PRT
<213> ORGANISM: Artificial Sequence
<220> FEATURE:
<223> OTHER INFORMATION: recombinant IFNtau based on Ovis aries sequence

<400> SEQUENCE: 4

Cys Tyr Leu Ser Glu Arg Leu Met Leu Asp Ala Arg Glu Asn Leu Lys
 1               5                  10                  15

Leu Leu Asp Arg Met Asn Arg Leu Ser Pro His Ser Cys Leu Gln Asp
            20                  25                  30

Arg Lys Asp Phe Gly Leu Pro Gln Glu Met Val Glu Gly Asp Gln Leu
        35                  40                  45

Gln Lys Asp Gln Ala Phe Pro Val Leu Tyr Glu Met Leu Gln Gln Ser
    50                  55                  60

Phe Asn Leu Phe Tyr Thr Glu His Ser Ser Ala Ala Trp Asp Thr Thr
65                  70                  75                  80

Leu Leu Glu Gln Leu Cys Thr Gly Leu Gln Gln Gln Leu Asp His Leu
                85                  90                  95

Asp Thr Cys Arg Gly Gln Val Met Gly Glu Glu Asp Ser Glu Leu Gly
            100                 105                 110

Asn Met Asp Pro Ile Val Thr Val Lys Lys Tyr Phe Gln Gly Ile Tyr
            115                 120                 125

Asp Tyr Leu Gln Glu Lys Gly Tyr Ser Asp Cys Ala Trp Glu Ile Val
        130                 135                 140

Arg Val Glu Met Met Arg Ala Leu Thr Val Ser Thr Thr Leu Gln Lys
145                 150                 155                 160

Arg Leu Thr Lys Met Gly Gly Asp Leu Asn Ser Pro
                165                 170
```